(12) United States Patent
Pacetti et al.

(10) Patent No.: US 7,795,467 B1
(45) Date of Patent: Sep. 14, 2010

(54) BIOABSORBABLE, BIOBENEFICIAL POLYURETHANES FOR USE IN MEDICAL DEVICES

(75) Inventors: Stephen Dirk Pacetti, San Jose, CA (US); Charles Claude, Sunnyvale, CA (US); Irina Astafieva, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1450 days.

(21) Appl. No.: 11/115,699

(22) Filed: Apr. 26, 2005

(51) Int. Cl.
*C07C 265/00* (2006.01)
*C07C 265/02* (2006.01)
*C07C 265/04* (2006.01)
*C07C 265/06* (2006.01)
*C07C 265/08* (2006.01)
*C07C 265/10* (2006.01)
*C07C 265/12* (2006.01)
*C07C 265/14* (2006.01)

(52) U.S. Cl. .................... 560/336; 560/354; 560/355; 560/358; 560/360

(58) Field of Classification Search .................... None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |

(Continued)

FOREIGN PATENT DOCUMENTS

DE   42 24 401   1/1994

(Continued)

OTHER PUBLICATIONS

Guan et al., "Preparation and characterization of highly porous, biodegradable polyurethane scaffolds for soft tissue applications" Biomaterials (2005) vol. 26 pp. 3961-3971.*

(Continued)

*Primary Examiner*—Eric S Olson
(74) *Attorney, Agent, or Firm*—Squire, Sanders & Dempsey L.L.P.

(57) ABSTRACT

Bioabsorbable, polyurethane-based stent coatings that comprise non-fouling coatings with polyethylene glycol and hyaluronic acid are disclosed. In addition to these coatings, medical devices comprising these coatings and methods of applying the coatings are disclosed.

37 Claims, No Drawings

U.S. PATENT DOCUMENTS

| | | | |
|---|---|---|---|
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,531,076 B2 * | 3/2003 | Crano et al. ............... 252/586 |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |

| | | | | | | |
|---|---|---|---|---|---|---|
| 6,673,385 B1 | 1/2004 | Ding et al. | | 2003/0083739 A1 | 5/2003 | Cafferata |
| 6,689,099 B2 | 2/2004 | Mirzaee | | 2003/0097088 A1 | 5/2003 | Pacetti |
| 6,695,920 B1 | 2/2004 | Pacetti et al. | | 2003/0097173 A1 | 5/2003 | Dutta |
| 6,706,013 B1 | 3/2004 | Bhat et al. | | 2003/0099712 A1 | 5/2003 | Jayaraman |
| 6,709,514 B1 | 3/2004 | Hossainy | | 2003/0105518 A1 | 6/2003 | Dutta |
| 6,712,845 B2 | 3/2004 | Hossainy | | 2003/0113439 A1 | 6/2003 | Pacetti et al. |
| 6,713,119 B2 | 3/2004 | Hossainy et al. | | 2003/0150380 A1 | 8/2003 | Yoe |
| 6,716,444 B1 | 4/2004 | Castro et al. | | 2003/0157241 A1 | 8/2003 | Hossainy et al. |
| 6,723,120 B2 | 4/2004 | Yan | | 2003/0158517 A1 | 8/2003 | Kokish |
| 6,733,768 B2 | 5/2004 | Hossainy et al. | | 2003/0190406 A1 | 10/2003 | Hossainy et al. |
| 6,740,040 B1 | 5/2004 | Mandrusov et al. | | 2003/0207020 A1 | 11/2003 | Villareal |
| 6,743,462 B1 | 6/2004 | Pacetti | | 2003/0211230 A1 | 11/2003 | Pacetti et al. |
| 6,749,626 B1 | 6/2004 | Bhat et al. | | 2004/0018296 A1 | 1/2004 | Castro et al. |
| 6,753,071 B1 | 6/2004 | Pacetti et al. | | 2004/0029952 A1 | 2/2004 | Chen et al. |
| 6,756,449 B2 * | 6/2004 | Benz et al. ............... 525/326.9 | | 2004/0047978 A1 | 3/2004 | Hossainy et al. |
| 6,758,859 B1 | 7/2004 | Dang et al. | | 2004/0047980 A1 | 3/2004 | Pacetti et al. |
| 6,759,054 B2 | 7/2004 | Chen et al. | | 2004/0052858 A1 | 3/2004 | Wu et al. |
| 6,764,505 B1 | 7/2004 | Hossainy et al. | | 2004/0052859 A1 | 3/2004 | Wu et al. |
| 6,861,088 B2 | 3/2005 | Weber et al. | | 2004/0054104 A1 | 3/2004 | Pacetti |
| 6,865,810 B2 | 3/2005 | Stinson | | 2004/0060508 A1 | 4/2004 | Pacetti et al. |
| 6,869,443 B2 | 3/2005 | Buscemi et al. | | 2004/0062853 A1 | 4/2004 | Pacetti et al. |
| 6,878,160 B2 | 4/2005 | Gilligan et al. | | 2004/0063805 A1 | 4/2004 | Pacetti et al. |
| 6,887,270 B2 | 5/2005 | Miller et al. | | 2004/0071861 A1 | 4/2004 | Mandrusov et al. |
| 6,887,485 B2 | 5/2005 | Fitzhugh et al. | | 2004/0072922 A1 | 4/2004 | Hossainy et al. |
| 6,890,546 B2 | 5/2005 | Mollison et al. | | 2004/0073298 A1 | 4/2004 | Hossainy |
| 6,899,731 B2 | 5/2005 | Li et al. | | 2004/0086542 A1 | 5/2004 | Hossainy et al. |
| 2001/0007083 A1 | 7/2001 | Roorda | | 2004/0086550 A1 | 5/2004 | Roorda et al. |
| 2001/0014717 A1 | 8/2001 | Hossainy et al. | | 2004/0096504 A1 | 5/2004 | Michal |
| 2001/0018469 A1 | 8/2001 | Chen et al. | | 2004/0098117 A1 | 5/2004 | Hossainy et al. |
| 2001/0020011 A1 | 9/2001 | Mathiowitz et al. | | 2005/0037052 A1 | 2/2005 | Udipi et al. |
| 2001/0029351 A1 | 10/2001 | Falotico et al. | | 2005/0038134 A1 | 2/2005 | Loomis et al. |
| 2001/0037145 A1 | 11/2001 | Guruwaiya et al. | | 2005/0038497 A1 | 2/2005 | Neuendorf et al. |
| 2001/0051608 A1 | 12/2001 | Mathiowitz et al. | | 2005/0043786 A1 | 2/2005 | Chu et al. |
| 2002/0005206 A1 | 1/2002 | Falotico et al. | | 2005/0049693 A1 | 3/2005 | Walker |
| 2002/0007213 A1 | 1/2002 | Falotico et al. | | 2005/0049694 A1 | 3/2005 | Neary |
| 2002/0007214 A1 | 1/2002 | Falotico | | 2005/0054774 A1 | 3/2005 | Kangas |
| 2002/0007215 A1 | 1/2002 | Falotico et al. | | 2005/0055044 A1 | 3/2005 | Kangas |
| 2002/0009604 A1 | 1/2002 | Zamora et al. | | 2005/0055078 A1 | 3/2005 | Campbell |
| 2002/0016625 A1 | 2/2002 | Falotico et al. | | 2005/0060020 A1 | 3/2005 | Jenson |
| 2002/0032414 A1 | 3/2002 | Ragheb et al. | | 2005/0064088 A1 | 3/2005 | Fredrickson |
| 2002/0032434 A1 | 3/2002 | Chudzik et al. | | 2005/0065501 A1 | 3/2005 | Wallace |
| 2002/0051730 A1 | 5/2002 | Bodnar et al. | | 2005/0065545 A1 | 3/2005 | Wallace |
| 2002/0071822 A1 | 6/2002 | Uhrich | | 2005/0065593 A1 | 3/2005 | Chu et al. |
| 2002/0077693 A1 | 6/2002 | Barclay et al. | | 2005/0074406 A1 | 4/2005 | Couvillon, Jr. et al. |
| 2002/0082679 A1 | 6/2002 | Sirhan et al. | | 2005/0074545 A1 | 4/2005 | Thomas |
| 2002/0087123 A1 | 7/2002 | Hossainy et al. | | 2005/0075714 A1 | 4/2005 | Cheng et al. |
| 2002/0091433 A1 | 7/2002 | Ding et al. | | 2005/0079274 A1 | 4/2005 | Palasis et al. |
| 2002/0094440 A1 | 7/2002 | Llanos et al. | | 2005/0084515 A1 | 4/2005 | Udipi et al. |
| 2002/0111590 A1 | 8/2002 | Davila et al. | | | | |
| 2002/0120326 A1 | 8/2002 | Michal | | | FOREIGN PATENT DOCUMENTS | |
| 2002/0123801 A1 | 9/2002 | Pacetti et al. | | | | |
| 2002/0142039 A1 | 10/2002 | Claude | | EP | 0 301 856 | 2/1989 |
| 2002/0155212 A1 | 10/2002 | Hossainy | | EP | 0 396 429 | 11/1990 |
| 2002/0165608 A1 | 11/2002 | Llanos et al. | | EP | 0 514 406 | 11/1992 |
| 2002/0176849 A1 | 11/2002 | Slepian | | EP | 0 604 022 | 6/1994 |
| 2002/0183581 A1 | 12/2002 | Yoe et al. | | EP | 0 623 354 | 11/1994 |
| 2002/0188037 A1 | 12/2002 | Chudzik et al. | | EP | 0 665 023 | 8/1995 |
| 2002/0188277 A1 | 12/2002 | Roorda et al. | | EP | 0 701 802 | 3/1996 |
| 2003/0004141 A1 | 1/2003 | Brown | | EP | 0 716 836 | 6/1996 |
| 2003/0028243 A1 | 2/2003 | Bates et al. | | EP | 0 809 999 | 12/1997 |
| 2003/0028244 A1 | 2/2003 | Bates et al. | | EP | 0 832 655 | 4/1998 |
| 2003/0031780 A1 | 2/2003 | Chudzik et al. | | EP | 0 850 651 | 7/1998 |
| 2003/0032767 A1 | 2/2003 | Tada et al. | | EP | 0 879 595 | 11/1998 |
| 2003/0036794 A1 | 2/2003 | Ragheb et al. | | EP | 0 910 584 | 4/1999 |
| 2003/0039689 A1 | 2/2003 | Chen et al. | | EP | 0 923 953 | 6/1999 |
| 2003/0040712 A1 | 2/2003 | Ray et al. | | EP | 0 953 320 | 11/1999 |
| 2003/0040790 A1 | 2/2003 | Furst | | EP | 0 970 711 | 1/2000 |
| 2003/0059520 A1 | 3/2003 | Chen et al. | | EP | 0 982 041 | 3/2000 |
| 2003/0060877 A1 | 3/2003 | Falotico et al. | | EP | 1 023 879 | 8/2000 |
| 2003/0065377 A1 | 4/2003 | Davila et al. | | EP | 1 192 957 | 4/2002 |
| 2003/0072868 A1 | 4/2003 | Harish et al. | | EP | 1 273 314 | 1/2003 |
| 2003/0073961 A1 | 4/2003 | Happ | | JP | 2001-190687 | 7/2001 |
| 2003/0083646 A1 | 5/2003 | Sirhan et al. | | SU | 872531 | 10/1981 |

| | | |
|---|---|---|
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Heijkants et al., "Design, Synthesis, and properties of a degradable polyurethane scaffold for meniscus regeneration" Journal of Materials Science: Materials in Medicine (2004) vol. 15 pp. 423-427.*
Mohaghegh et al., "Synthesis and Characterization of N-polyethylene glycom monomethyl ether substituted polyurethane (PU)" Iranian Polymer Journal (2005) vol. 14 No. 9, pp. 815-821.*
Mazid et al., "New Biocompatible Polyurethane-Type Copolymer with Low Molecular Weight Heparin" Clinical Materials (1991) vol. 8 pp. 71-80.*
Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Guan et al., *Synthesis, characterization, and cytocompatibility of elastomeric, biodegradable poly(ester-urethane)ureas based on poly(caprolactone) and putrescine*, J. Biomat. Res., pp. 493-503 (2002).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Woo et al., *Synthesis and characterization of a novel biodegradable antimicrobial polymer*, Biomaterials, vol. 21, pp. 1235-1246 (2000).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

BIOABSORBABLE, BIOBENEFICIAL POLYURETHANES FOR USE IN MEDICAL DEVICES

BACKGROUND

Percutaneous transluminal coronary angioplasty (PTCA) is a procedure for treating heart disease. A physician introduces a catheter assembly, having a balloon portion, percutaneously into the cardiovascular system of a patient via the brachial or femoral artery. The physician advances the catheter assembly through the coronary vasculature until the balloon portion crosses the occlusive lesion. Once in position, the physician inflates the balloon to radially compress the atherosclerotic plaque of the lesion and remodel the vessel wall. The surgeon then deflates the balloon to remove the catheter.

However, this procedure can create intimal flaps and tear arterial linings, which can collapse and occlude the vessel after balloon removal. Moreover, thrombosis and restenosis of the artery may develop over several months following the procedure, which may require another angioplasty procedure or a by-pass operation. To reduce arterial occlusion, thrombosis, and restenosis, the physician can implant a stent into the vessel.

Physicians use stents mechanically and to provide biological therapy. Mechanically, stents act as scaffoldings, physically holding open and, if desired, expanding the vessel wall. Typically, stents compress for insertion through small vessels and then expand to a larger diameter once in position. U.S. Pat. No. 4,733,665, issued to Palmaz; U.S. Pat. No. 4,800,882, issued to Gianturco; and U.S. Pat. No. 4,886,062, issued to Wiktor disclose examples of PTCA stents.

Medicating the stent provides for pharmacological therapy. Medicated stents allow local drug administration at the diseased site. To provide an effective drug concentration at a site, systemic treatment often requires concentrations that produce adverse or toxic effects. Local delivery advantageously allows for smaller systemic drug levels in comparison to systemic treatment. Because of this, local delivery produces fewer side effects and achieves results that are more favorable. One proposed method for medicating stents involves coating a polymeric carrier onto a stent surface. This method applies a solution that includes a solvent, a dissolved polymer, and a dissolved or dispersed drug to the stent. As the solvent evaporates, it leaves a drug-impregnated polymer coating on the stent.

Current biomaterials research aims at controlling protein adsorption on implantable medical devices. Current biomaterials typically exhibit uncontrolled protein adsorption, leading to a mixed layer of partially denatured proteins. Current surfaces contain different cell binding sites resulting from adsorbed proteins such as fibrinogen and immunoglobulin G. platelets and inflammatory cells such as macrophages and neutrophils adhere to these surfaces. When activated, these cells secret a wide variety of pro-inflammatory and proliferative factors. Non-fouling surfaces control these events, and absorb little or no protein, primarily due to their hydrophilicity. One prior art approach creates these surfaces by using hyaluronic acid or polyethylene glycol. Non-fouling surfaces or coatings are a subset of biobeneficial coatings, which are coatings that benefit the treatment site without necessarily releasing pharmaceutically or therapeutically active agents ("drug(s)"). Another type of biobeneficial coating contains free-radical scavengers, which preserve nitric oxide and prevent oxidative damage.

Biobeneficial coatings provide surfaces that can have a biological benefit without the release of pharmaceutically active agents. Although an otherwise biobeneficial coating could release such active agents, if that were desired. The world of biobeneficial coatings may be divided into two categories, those that are intended to be bioabsorbable, and those that are intended to be biostable. Desirable properties for bioabsorbable, biobeneficial coatings include any of the following properties:

Improved bioactivity in-vitro and in-vivo, measured by
    platelet adhesion
    protein binding
    inflammatory response
    acceleration of healing
Improved mechanical properties, measured by
    minimal cracking on expansion
    resistance to damage from crimping and heat and pressure stent-catheter attachment processes
    balloon shear resistance
Improved bioabsorption rate, measured by
    slow enough degradation to minimize inflammatory response
    slow enough degradation to capture some biobeneficial benefit
    fast enough degradation to substantially completely degrade in an accessible time (preferably less than 6 months)

One suitable polymer family useful with medical devices is polyurethanes. Polyurethanes are a broad family of elastomeric materials. A subset of these materials, thermoplastic elastomers, has served in medical devices for decades. Polymer properties, such as flexibility, high elongation, fatigue resistance, and blood compatibility, have driven polyurethane medical applications. A current topic in drug eluting stents is polymeric coatings that hold the drug, control its release, and bioabsorb with little or no inflammatory response. Polyurethanes are not usually considered bioabsorbable polymers because they contain a hydrolytically stable urethane linkage. While physiologic enzymes can cleave the urethane linkage, there is no evidence that this leads to complete bioabsorption. (G. L. Y. Woo et al. Biomaterials 21 (2000) 1235-1246.)

Moreover, urethane cleavage in aromatic-diisocyanate-based polyurethanes releases aromatic diamines, which can be carcinogenic. Using diisocyanates that would degrade to endogenous diamines or fragments that are identical to or similar to endogenous diamines avoids aromatic diamine release. Along those lines, Wagner has taken steps to develop bioabsorbable polyurethanes. (J. Guan, M. S. Sacks, E. J. Beckman, W. R. Wagner, J. Biomat. Res. 2002, 493-503.) Ways to improve their biocompatibility, modify the drug release rate via increased hydrophilicity, and increase their number and type are described below. Incorporating hydrolytically labile groups into the polymer backbone alters polyurethane biodegradability. Esters are an example of hydrolytically labile groups that may be incorporated into the polyurethane polymer backbone.

SUMMARY

A family of bioabsorbable, non-fouling, or biobeneficial polyurethanes useful in drug eluting stent coatings is disclosed. These materials are polyurethanes that, due to their hard-versus-soft-segment morphology, will behave as thermoplastic elastomers. These polymers can be synthesized from the components described below.

Some invention embodiments can be described as a composition comprising the polymerization product of an A-moiety derived from a diisocyanate, a B-moiety derived from a chain extender, and a C-moiety derived from a biobeneficial moiety. In these or other embodiments, the composition can have at least one block as represented by the following formulas:

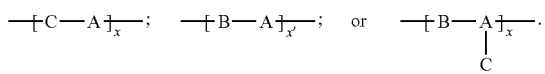

In theses blocks, numerals x or x' are integers from 1-50,000, A represents an A-moiety, B represents a B-moiety, and C represents a C-moiety. In these or other embodiments, the biobeneficial-containing blocks can be represented by the formulas

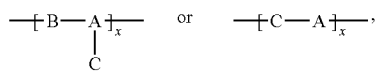

linking blocks can be represented by the formula,

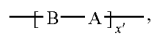

and the composition comprises at least one biobeneficial-containing block and at least one linking block.

In these or other embodiments, the composition is represented by one of Formula I-Formula VII, below.

In these or other embodiments, the diisocyanate is selected such that the hydrolysis product of the diisocyanate is a biocompatible diamine. And in these or other embodiments, the diisocyanate is an aliphatic diisocyanate, such as 1,4-diisocyanatobutane, 1,2-diisocyanatoethane, lysine ester diisocyanate, 1,5-diisocyanatopentane, or any combination of these.

In these or other embodiments, the biobeneficial moiety is connected to a hydroxyacid, a hydroxyacid composition, a hydroxyacid oligomer, an amino acid, an amino acid composition, or an amino acid oligomer. In some embodiments, the biobeneficial moiety is poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), such as R7, phosphoryl choline, heparin, chondroitan sulfate, glycosaminoglycans, chitosan, polyethylene oxide, or any combination of these.

In these or other embodiments, the chain extender is biocompatible. In some embodiments, the chain extender comprises an alcohol-amine, a diamine, a diol, a dithiol, or any combination of these. The diamine can be selected from 1,4-butanediamine, lysine ester, 1,2-ethanediamine, arginine ethyl ester, 1,5-pentanediamine, or any combination of these. The diol can be selected from 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, poly(caprolactone) diol, or any combination of these.

In these or other embodiments, the A-moiety is derived from a compound with a formula

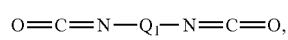

the B-moiety is derived from a compound with a formula, $W_2$-$Q_2$-$W_1$, and the C-moiety is derived from a compound with a formula A1-BB-A2, wherein Q1 and Q2 independently represent 1-50 carbon atom moieties, W1 and W2 independently represent O-, S-, or N-containing groups, A1 and A2 independently represent 1-20 carbon-atom hydroxy acids, hydroxy acid oligomers, amino acid, or amino acid oligomers, and BB represents a biobeneficial moiety. In these or other embodiments, Q1 and Q2 independently represent 1-20 carbon atom moieties. In these or other embodiments, W1 and W2 independently represent —OH or —NH$_2$. In these or other embodiments, A1 and A2 independently represent bioabsorbable hydroxy-acid radicals, a metabolic precursor to bioabsorbable hydroxy-acid radicals, bioabsorbable amino acid radicals, or a metabolic precursor to bioabsorbable amino acid radicals.

In these or other embodiments, the composition has Formula XXIII, Formula XXVI, Formula XXVII, Formula XXX, or

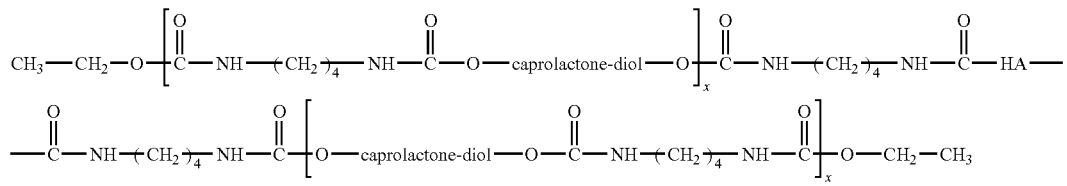

wherein x is an integer greater than or equal to 1, x' is an integer greater than or equal to 1, y is integer greater than or equal to 1, HA represents a hyaluronic acid or hyaluronic acid derivative, and mPEG represents a methoxy-poly(ethylene glycol) moiety.

In these or other embodiments, the composition can be described as comprising an A-moiety derived from a diisocyanate, wherein the diisocyanate is 1,4-diisocyanatobutane, 1,2-diisocyanatoethane, lysine ester diisocyanate, 1,5-diisocyanatopentane, or any combination of these, a B-moiety derived from a chain extender comprising an alcohol-amine, diamine, diol or any combination of these wherein the diamine or diol is 1,4-butanediamine, Lysine Ester, 1,2-ethanediamine, Arginine Ethyl Ester, 1,5-pentanediamine, 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, caprolactone diol, or any combination of these, and a C-moiety derived from a biobeneficial moiety comprising poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), such as R7, phosphoryl choline, heparin, chondroitan sulfate, glycosaminoglycans, chitosan, polyethylene oxide, or any combination of these, and a hydroxyacid selected from 2-hydroxyacids, 3-hydroxy acids, 4-hydroxy acids, or c-hydroxy-caproic acid, oligomers of the above, or any combination of these; or the amino acid is glycine, valine, leucine, isoleucine, proline, phenylalanine, oligomers of the above, or any combination of these, wherein the biobeneficial moiety has a maximum molecular weight of 40,000±4,000 Daltons, as discussed below.

In some embodiments, the invention relates to a medical device comprising at least one type-one polymer, wherein type-one polymers are the compositions described above. In some embodiments, the medical device has one of the above-described polymers coated onto the surface of the device to form a layer of polymer. In some embodiments, another type-one polymer is disposed on the polymer layer.

Some medical device embodiments comprise a composition, as described above and further comprise a type-two polymer, wherein type-two polymers are biocompatible and are selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. Some medical device embodiments that comprise a type-one and a type-two polymer further comprise at least one inner layer and one outer layer wherein the inner layer is a type-two polymer and the outer layer is a type-one polymer; or the inner layer is a type-one polymer and the outer layer is a type-two polymer.

In these or other embodiments, the medical device further comprises a therapeutic agent. The following types of therapeutic agents are found in some invention embodiments: proteins, peptides, antiproliferatives, antineoplastics, antiinflammatories, antiplateletes, anticoagulants, antifibrins, antithrombins, antimitotics, antibiotics, antioxidants, or their mixtures.

Embodiments according to the current invention can be described as methods of making invention compositions. For instance, some invention methods comprise reacting an amount of hydroxy-acid- or amino-acid-modified biobeneficial composition with an amount of diisocyanate to yield an intermediate and reacting the intermediate with a chain extender. In these or other embodiments, the amount of hydroxy-acid- or amino-acid-modified biobeneficial composition ranges from 0.1 mole % to 100 mole % of the amount of diisocyanate or ranges from 0.1 weight % to 100 weight % of the amount of diisocyanate; alternatively, the amount of hydroxy-acid- or amino-acid-modified biobeneficial composition ranges from 0.33 mole % to 3 mole % of the amount of diisocyanate or ranges from 0.33 weight % to 3 weight % of the amount of diisocyanate.

DETAILED DESCRIPTION

A "non-fouling moiety" is a portion of a chemical compound that is capable of providing the compound with the ability to prevent or at least reduce the build-up of a denatured layer of protein on the stent surface or on the stent coating. It is a type of bioactive moiety and a type of biobeneficial moiety.

"Biobeneficial coatings" benefit the treatment site without necessarily releasing pharmaceutically or therapeutically active agents (drug(s)).

"Biodegradable" means that a substance is not hydrolytically, oxidatively, or enzymatically stable and is substantially broken down by the in vivo environment in an amount of time of from 1 to 24 months; alternatively, in an amount of time of from 2 to 18 months; alternatively, in an amount of time of from 3 to 12 months. For purposes of this disclosure, substantially broken down means that non-invasive diagnostic procedures as skilled artisans normally employ cannot detect the polymer in vivo. This can be confirmed by use of appropriate in vivo animal models, which allow the implant to be removed and analyzed at serial time points. A way of testing biodegradability is to immerse the substance in a solution that mimics the in vivo environment and monitor its mass loss over time. If the material has lost more than 5%, 10%, 15%, 20%, 40%, 50%, 60%, 70%, or 80% of its mass over a 6-month period, then it can be characterized as biodegradable.

Generally, "biocompatible" takes its standard meaning as known to those of ordinary skill in the art. For some embodiments, "biocompatible" means that the material passes or is found acceptable by at least one of the following in vitro tests, as specified by ISO 10993. In some embodiments, these in vitro tests would include ISO 10993-5 cytotoxicity (this is a L929 mouse fibroblast test using extracts of the material); ISO 10993-4 hemocompatibility (this is a specific test for thrombosis, coagulation, platelet consumption, hematology, and immunology); ISO 10993-3 genotoxicity (this includes the Ames test, mouse cell lymphoma test, Chinese hamster ovary cell test); or a combination of these.

"Unbranched" means that a polymer has less than 0.1 mole percent of sidechains having more than 10 atoms; alternatively, less than 0.01 mole percent of such sidechains; alternatively, less than 0.001 mole percent of such sidechains.

"Branched" means that a polymer has greater than 0.1 mole percent of sidechains having more than 10 atoms; alternatively, greater than 0.01 mole percent of such sidechains; alternatively, greater than 0.001 mole percent of such sidechains.

"Uncrosslinked" means that a polymer sample contains less than or equal to 0.1 mole percent of cross-linked polymers; alternatively, invention polymers or compositions have less than 0.01 mole percent of cross-linked polymers; alternatively, invention polymers or compositions have less than 0.001 mole percent of cross-linked polymers.

"Crosslinked" means that a polymer sample contains greater than 0.1 mole percent of connections between two polymer chains; alternatively, greater than 0.01 mole percent connections between two polymer chains; alternatively, greater than 0.001 mole percent of connections between two polymer chains.

"Partially cross-linked" means having greater than 0.001 mole percent and less than 0.1 mole percent of cross-linked polymers.

"Hydrolytically unstable", "unstable to hydrolysis", or "susceptible to hydrolysis" are defined as the characteristic of a compound (e.g., a polymer or a polymeric adduct) such that when exposed to aqueous fluids having pH near neutral (e.g., blood), the compound can be substantially hydrolyzed within 0 to 24 months, 0 to 12 months, 0 to 6 months, or 0 to 1 month. The temperature of an aqueous liquid to which a compound is exposed can be between room temperature and 37° C.

"Substantially hydrolyzed" is defined as losing 95 or more percent, 75 or more percent, 50 or more percent, 40 or more percent, or 20 or more percent of the polymer (by mass) to hydrolysis.

"Oxidatively unstable", "unstable to oxidation", or "susceptible to oxidation" are defined as the characteristic of a compound (e.g., a polymer or a polymeric adduct) such that when exposed to superoxide anion, ozone, hydrogen peroxide, or hypochlorite anion in aqueous fluids having pH near neutral (e.g., blood), the compound has linkages that can be substantially cleaved within 0 to 24 months, 0 to 12 months, 0 to 6 months, or 0 to 1 month. The temperature of an aqueous liquid to which a compound is exposed can be between room temperature and 37° C. "Substantially oxidatively cleaved" is defined as losing 95 or more percent, 75 or more percent, 50 or more percent, 40 or more percent, or 20 or more percent of the polymer (by mass) to oxidation.

"Unstable to enzymes", or "susceptible to enzymolysis" are defined as the characteristic of a compound (e.g., a polymer or a polymeric adduct) such that when exposed to enzymes found in vivo such as serine proteases, chymotrypsin, peptidases, pepsin, or matrix metalloproteinases in aqueous fluids having pH near neutral (e.g., blood), linkages within the compound can be substantially cleaved within 0 to 24 months, 0 to 12 months, 0 to 6 months, or 0 to 1 month. The temperature of an aqueous liquid to which a compound is exposed can be between room temperature and 37° C. "Substantially enzymatically cleaved" is defined as losing 95 or more percent, 75 or more percent, 50 or more percent, 40 or more percent, or 20 or more percent of the polymer (by mass) to enzymatic action.

One way of determining whether a polymer or a polymeric adduct is hydrolytically stable includes (a) depositing the polymer or adduct on a stent to make a polymer-coated stent; (b) weighing the polymer-coated stent; (c) immersing the polymer-coated stent into an aqueous fluid having pH near neutral; and (d) periodically weighing the stent. Alternatively, if the stent is predominately the target polymer or polymeric adduct then determining hydrolytic stability includes (a) preparing the stent from the polymer or adduct; (b) weighing the polymeric stent; (c) immersing the stent into an aqueous fluid having pH near neutral; and (d) periodically weighing the stent. If, after exposure for enough time to meet the above time definitions, little enough polymer or adduct remains on the stent to meet the above mass percent definitions, the polymer or adduct is defined as "hydrolytically unstable". Likewise, if little enough of the stent remains to meet the above mass percent definitions, the polymer or adduct is also defined as "hydrolytically unstable."

One way of determining whether a polymer or a polymeric adduct is oxidatively stable includes (a) depositing the polymer or adduct on a stent to make a polymer-coated stent; (b) weighing the polymer-coated stent; (c) immersing the polymer-coated stent into an aqueous fluid having pH near neutral containing an oxidant such as superoxide anion, hydrogen peroxide, or hypochlorite anion; and (d) periodically weighing the stent. Alternatively, if the stent is predominately the target polymer or polymeric adduct then determining oxidative stability includes (a) preparing the stent from the polymer or adduct; (b) weighing the polymeric stent; (c) immersing the stent into an aqueous fluid having pH near neutral containing an oxidant; and (d) periodically weighing the stent. If, after exposure for enough time to meet the above time definitions, little enough polymer or adduct remains on the stent to meet the above mass percent definitions, the polymer or adduct is defined as "oxidatively unstable". Likewise, if little enough of the stent remains to meet the above mass percent definitions, the polymer or adduct is also defined as "oxidatively unstable".

One way of determining whether a polymer or a polymeric adduct is enzymatically stable includes (a) depositing the polymer or adduct on a stent to make a polymer-coated stent; (b) weighing the polymer-coated stent; (c) immersing the polymer-coated stent into an aqueous fluid having pH near neutral containing an appropriate enzyme such as a serine protease, peptidase, pepsin, or matrix metalloproteinase; and (d) periodically weighing the stent. Alternatively, if the stent is predominately the target polymer or polymeric adduct then determining enzymatic stability includes (a) preparing the stent from the polymer or adduct; (b) weighing the polymeric stent; (c) immersing the stent into an aqueous fluid having pH near neutral containing an appropriate enzyme; and (d) periodically weighing the stent. If, after exposure for enough time to meet the above time definitions, little enough polymer or adduct remains on the stent to meet the above mass percent definitions, the polymer or adduct is defined as "enzymatically unstable". Likewise, if little enough of the stent remains to meet the above mass percent definitions, the polymer or adduct is also defined as "enzymatically unstable".

Depending upon the reaction sequence and/or relative reactivity of the monomers, invention polymers or compositions can be more random-like or more block-like. Sometimes, the degree of "randomness" or "blockness" is generically referred to as polymer topology. For purposes of this disclosure, a polymer is characterized as having a more random-like topology if the number of adjacent A-moieties, B-moieties, or C-moieties is small, such as less than 90% for at least one of these blocks or such as less than 75% for at least one of these blocks; for purposes of this disclosure, a polymer has a random topology if at least one of these blocks has less than 50% adjacent blocks. For purposes of this disclosure, a polymer is characterized as having a more block-like topology if the number of adjacent A-moieties, B-moieties, or C-moieties is large, such as greater than 25% for at least one of these moieties or such as greater than 50% for at least one of these moieties. For purposes of this disclosure, a polymer has a block topology if at least one of these moieties has greater than 75% adjacent moieties.

If the particular discussion of a polymer is silent regarding polymer topology, that discussion encompasses embodiments with a polymer topology selected from all topologies, random-like topologies, block-like topologies, random topologies, block topologies, and topologies intermediate between random-like and block-like topologies. Moreover, in some embodiments the polymer is selected to exclude polymers with topologies selected from random-like, block-like, random, block, topologies intermediate between random-like and block-like, or any combination of these topologies.

For purposes of this disclosure, "modulate biological outcome" means adjusting the polymer biobeneficial-component content in order to substantially decrease fibrinogen absorption, platelet binding, the number of adherent macrophages and inflammatory cells, and the degree of inflammatory cell activation. In some embodiments, "substantially decrease" means that the decrease is large enough to commercially warrant any added cost of using invention compositions, polymers, or methods. In these or other embodiments, "substantially decrease" means a 10, 20, 40, 50, 60, 70, 80, 90, or 99% decrease.

The general formula for some embodiments of polymers according to the current invention can be represented by Formula I-Formula VII.

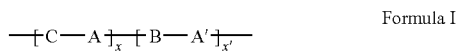

Formula I wherein x, x', x", and x'" are integers of 1-50,000; A, A', A", and A'" independently represent A-moieties, B, B', B", and B'" independently represent B-moieties; and C, C', C", and C'" independently represent C-moieties. One of ordinary skill in the art recognizes that many permutations of the various A-, B-, and C-moieties exist.

The structure shown below represents an invention polymer or composition.

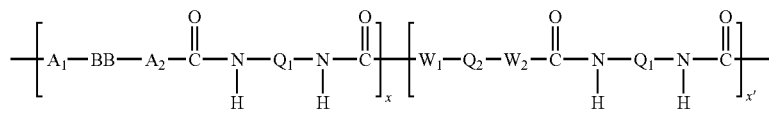

wherein

A1 and A2 independently represent 1-20 carbon-atom hydroxy-acid or amino acid radicals;

Q1 and Q2 independently represent 1-50 carbon atom moieties;

W1 and W2 independently represent O-, S-, or N-containing groups;

BB represents a biobeneficial moiety; and

Numerals x and x' are integers from 1 to 50,000.

A-moiety, Diisocyanate

As described earlier, a diisocyanate can be used. In some embodiments, the diisocyanate is (un)branched aliphatic, cycloaliphatic, or aromatic. In vivo, when these biodegradable urethanes break down, the diisocyanate component is released as a diamine. In instances where the utility of the urethane requires that a particular aliphatic, cycloaliphatic, or aromatic amine not be present, the A-moiety is defined to exclude a diisocyanate that breaks down into the undesired amine. In some embodiments, only certain aliphatic diisocyanates yield biocompatible break-down products. In some embodiments, the diisocyanate is chosen to exclude those comprising aromatic groups. Some embodiments specifically exclude any one or any combination of branched or unbranched aliphatic, cycloaliphatic, or aromatic diisocyanates.

A generic diisocyanate is shown in Formula IX, below.

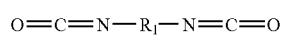

Formula VIII

A useful, butane-based diisocyanate is depicted below in Formula IX. This diisocyanate is 1,4-diisocyanatobutane. When it degrades in vivo, it releases 1,4-butanediamine (putrescine). Putrescine is endogenous, is biocompatible, and has been identified as a cell growth and differentiation mediator.

Formula IX

Another useful, ethane-based diisocyanate is depicted below in Formula X. This diisocyanate releases ethylene diamine when it degrades in vivo. Ethylene diamine has been used in several bioabsorbable poly(ester amides). It is also unlikely that biodegradation of the poly(ester amide) polymer will predominantly yield free diamines. One of ordinary skill in the art expects the ester linkages to cleave first, releasing diffusible degradation products that still contain the amide bond.

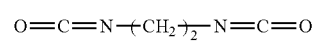

Formula X

Another diisocyanate useful for biodegradable polymers, because it degrades to release lysine, is the lysine ester diisocyanate shown below in Formula XI in the form of an ethyl ester.

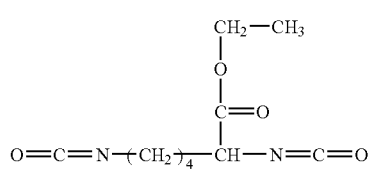

Formula XI

Other lysine esters are possible, and, in various embodiments, the substituent of the carboxyl can be selected from any 1-16-carbon-atom, branched, or linear, moieties.

In some embodiments, 1,5-diisocyanate serves as the A-moiety because it degrades to 1,5-pentanediamine, also known as cadaverene, which is a naturally occurring amine.

B-Moiety, Diamine, Diol, Hydroxyl-Amine, or Amine-Diamine Chain Extender

Generally, chain extenders are molecules with two or more functional groups linked by a relatively short-chain, (un) branched hydrocarbon or hydrocarbon derivative. The short-chain hydrocarbon derivatives can be selected from 1-50-carbon-atom moieties, 1-20-carbon-atom moieties, 1-15-carbon-atom moieties, 2-15-carbon-atom moieties, or 3-10-carbon-atom moieties. Additionally, some embodiments select short-chain hydrocarbon derivatives from groups that exclude any one or any combination of 1-50-carbon-atom moieties.

Each functional group should be selected such that it can react with the diisocyanate that attaches to the hydroxyl or amine-modified biobeneficial moiety. Several useful diamine or diol chain extenders may be used. A generic diamine is shown in Formula XII, below. Specific examples of useful diamine chain extenders, B-moieties, are 1,4-butanediamine (putrescine) (Formula XIII); 1,2-ethanediamine (Formula XIV); 1,5-pentanediamine (Formula XV); Lysine Ester (Formula XVI); Arginine Ester (Formula XVII); and their mixtures. Some embodiments specifically exclude any one or any combination of these diamines.

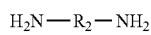
Formula XII

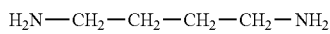
Formula XIII

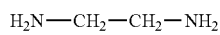
Formula XIV

Formula XV

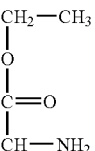
Formula XVI

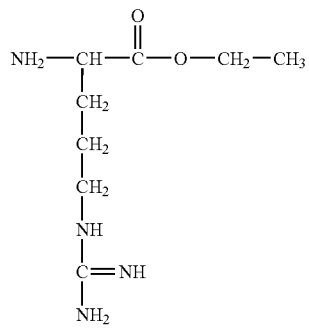
Formula XVII

R1 and R2, above and R3, shown below, are independently selected from (un)branched, 1-24-carbon-atom moieties. Many of these chain extenders are the hydrolysis products of the diisocyanates listed in the previous section. Putrescine and lysine ester are useful chain extenders due to their low toxicity and biocompatibility. Next, there are several diols with a history of use in bioabsorbable polymers. The first one depicted is a generic diol, in Formula XVIII.

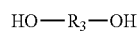
Formula XVIII

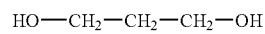
Formula XIX

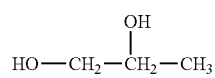
Formula XX

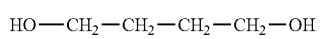
Formula XXI

Useful diols include 1,3-propanediol, 1,2-propanediol, 1,4-butanediol, 1,6-hexanediol, 1,10-decanediol, cyclohexanedimethanol, and poly(caprolactone)diol. Other potential diols are, 1,5-pentanediol, 1,4-cyclohexanediol, 1,7-heptanediol, 1,8-octanediol, 1,9-nonanediol, 1,12-dodecanediol, and caprolactone diol. Some embodiments specifically exclude any one or any combination of these diols.

Cyclohexanedimethanol diol has the advantage of being very rigid, thus raising the glass transition temperature (Tg) of the poly(urethane) hard segment.

The chain extenders that are amine-alcohol chain extenders can be thought of as any of the above diols or diamines in which an amine group replaces a single alcohol group in a diol or an alcohol group replaces a single amine group in a diamine.

An amine-diamine or diamine-amine is a chain extender with two amines near one end of the molecule and one amine near another end of the molecule.

C-Moiety, Polyester Modified Biobeneficial Moiety

This component contains a biobeneficial or non-fouling moiety connected to a hydroxy acid, such as lactic acid to make diol-containing ester groups, or connected to an amino acid. The non-fouling moieties may be poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), such as R7, phosphoryl choline, heparin, chondroitan sulfate, glycosaminoglycans, chitosan, polyethylene oxide, or any combination of these. In some embodiments, the biobeneficial moiety is selected such that it excludes any one or any combination of the foregoing moieties.

In some embodiments, the maximum molecular weight of this component is selected to be low enough so that this component is small enough for the kidneys to release. In this respect, 40,000 Daltons is the maximum molecular weight for some embodiments. In other embodiments, 20,000 Daltons is the maximum molecular weight. If, upon release, the biobeneficial agent breaks down in the body, and then the molecular weight could be greater than about 40,000 Daltons without compromising patient safety.

PLURONIC polyols (PEO-PPO) are biologically compatible oligomeric or polymeric substances which are various brands of poly(ethylene oxide-co-propylene oxide) having the general formula $HO[-CH_2-CH_2-O-]_x[CH_2-CH_2-CH_2-O-]_y[-CH_2-CH_2-O-]_xH$. PLURONIC polyols are manufactured by BASF Corp. of Parsippany, N.J. and can have a molecular weight within a range of about 950 and about 4,000 Daltons, typically, about 1,750 and about 3,500 Daltons. "x" and "y" in the formula of PLURONIC shown above are integers selected in such a way that the terminal hydrophilic fragments (the "x" units) comprise between about 50 and about 70% (by mass) of the compound.

Hyaluronic acid is a linear polysaccharide composed of disaccharide units of N-acetylglucosamine and D-glucoronic acid, having a relatively high molecular weight. Silk-elastin protein block-copolymers combine the repeating blocks of amino acids thus providing the copolymer with the mechanical strength characterizing silk and the flexibility characterizing elastin. Silk-elastin block-copolymer can be obtained from Protein Polymer Technologies, Inc. of San Diego, Calif.

The hydroxy acid molecules may be, for example, 2-hydroxyacids, such as lactic acid or glycolic acid; 3-hydroxy acids such as 3-hydroxybutyric acid, 3-hydroxyvaleric acid, 3-hydroxypropanoic acid, or 3-hydroxyhexanoic acid; 4-hydroxy acids, such as 4-hydroxybutyric acid, 4-hydroxy valeric acid, 4-hydroxyhexanoic acid; or ε-hydroxy-caproic acid. The previous list is by way of example only. Some embodiments comprise hydroxy acids selected from groups defined as containing all hydroxy acid molecules excluding any one of or any combination of hydroxy acid molecules or excluding the hydroxy acid molecules specifically named above. Compositions that comprise hydroxy acid molecules or derivatives are sometimes referred to throughout this document as a hydroxy acid composition. A hydroxy acid composition is said to be "connected" to another moiety when a physical or chemical interaction causes the two to be substantially paired. An example of "connected" in this sense is a chemical bond between the hydroxy acid composition and the other moiety. Some embodiments employ a biobeneficial moiety connected to a hydroxy acid composition.

A-BB-A    Formula XXII

Formula XXII represents an exemplar of a C-moiety. In this formula, A represents a hydroxyacid moiety and BB represents a bioactive or non-fouling moiety.

A useful example for BB would be PEG that has been reacted with two equivalents of cyclic D,L-lactide as shown below in Formula XXIII. Regardless of the actual polymerization method, this compound can be thought of as arising from dehydrating a mixture of PEG with two equivalents of a lactide.

Formula XXIII

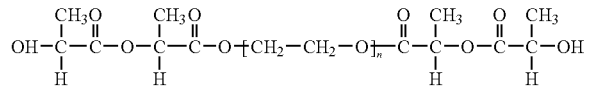

In addition to hydroxy acids being used to modify the bioactive or non-fouling moiety, amino acids may be used, as well. The amino acid may be, for example, glycine, alanine, valine, leucine, isoleucine, and other amino acids if the functionalities present in the molecule other than the amino and carboxyl groups are protected. The previous list is by way of example only. Some embodiments comprise amino acids selected from groups defined as containing all amino acid molecules excluding any one of or any combination of amino acid molecules or excluding the amino acid molecules specifically named above.

Compositions that comprise amino acid molecules or derivatives are sometimes referred to throughout this document as an amino acid composition. An amino acid composition is said to be "connected" to another moiety when a physical or chemical interaction causes the two to be substantially paired. An example of "connected" in this sense is a chemical bond between the amino acid composition and the other moiety. Some embodiments employ a biobeneficial moiety connected to an amino acid composition.

A-BB-A

Formula XXIV

Formula XXIV, A represents an amino acid moiety and BB represents a bioactive or non-fouling moiety. A useful example would be PEG that has been reacted with two equivalents of leucine as shown below. Regardless of the actual polymerization method, this compound can be thought of as arising from dehydrating a mixture of PEG with two equivalents of leucin.

Formula XXV

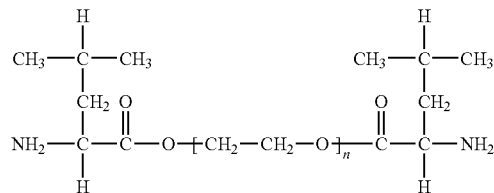

In Formula XXV, the amino acid-PEG conjugate is typically used as a salt, such as the di-p-toluene sulfonic acid salt.

In some embodiments, x is greater than or equal to 5 and less than or equal to 1200; alternatively, x is greater than or equal to 50 and less than or equal to 500. And x' is greater than or equal to 40 and less than or equal to 1500; alternatively, x' is greater than or equal to 100 and less than or equal to 750.

These invention polymers or compositions can be synthesized by a variety of methods. Starting with a hydroxyl-functional biobeneficial moiety, the adduct with a hydroxyl acid can be made by ring opening addition with the appropriate cyclic lactone. This reaction is typically catalyzed by zinc metal or by Lewis acid catalysts such as tin (II) 2-ethylhexanoate, tin alkoxides, and lanthanide alkoxides. The lactone addition can also be done by anionic ring opening that can be catalyzed by alkali metal alkoxides and crown ethers. These reactions are typically done under anhydrous conditions. To make the amino acid adduct with the hydroxyl function biobeneficial moiety, a straight forward approach is to use acid-catalyzed esterification. This can be performed under dehydrating conditions in a solvent such as benzene, toluene, or chloroform using an acid catalyst such as p-toluenesulfonic acid, trifluoroacetic acid, or sulfuric acid. The water formed can be distilled off as an azeotrope and collected using a Dean-Stark trap. If the biobeneficial moiety is amino functional, then addition to a hydroxyl acid can be made via a coupling reagent such as a carbodiimide. Coupling an amino functional biobeneficial moiety to an amino acid is more complex, as it can require the amino group on the amino acid to be protected. After the carbodiimide mediated coupling, the now-terminal amino group is formed by removal of the protecting group. These techniques are standard and known in peptide chemistry.

The polymerizations using the diisocyanates can be performed using techniques known in polyurethane chemistry. Good urethane polymerization solvents are dimethylsulfoxide, dimethylacetamide, dimethylformamide, tetrahydrofuran, 1,4-dioxane, and methylene chloride. Anhydrous conditions are required as water consumes isocyanate groups. Some embodiments select all-aliphatic diisocyanates as useful catalysts for the polymerization are Lewis acids, typically tin salts such as tin (II) 2-ethylhexanoate and dibutyltin dilaurate. As described earlier, these polymerizations can be one step where the functionalized biobeneficial moiety, diisocyanate, and diol or diamine chain extender are reacted all at once. Or the reaction may be stepwise with the biobeneficial moiety reacted first with diisocyanate, and the chain extender added later. In the two-step reaction, the stoichiometric amount of diisocyanate may be added initially, or a portion may be added in the second step with the chain extender.

A specific example of an invention polymer or composition comprising blocks that originate from 1,4-diisocyanatobutane, PEG-lactide, and 1,4-diaminobutane can be seen, below, in Formula XXVI.

Compared to Formula XXVI, this polymer will be softer because it lacks urea or urethane linkages. Its hard segments will be less hydrophobic, less crystalline, and more water absorbitive. Keeping other variables constant, it should Formula XXVI

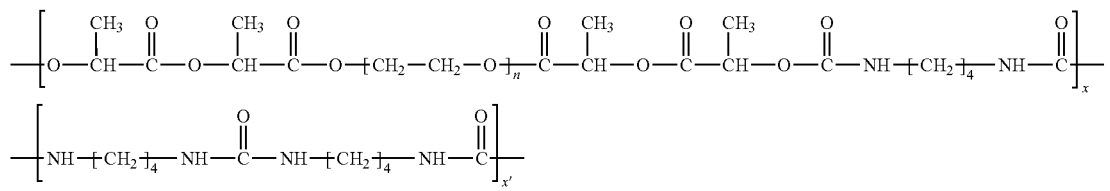

In some embodiments, n is greater than or equal to 4 and less than or equal to 450; alternatively, n is greater than or equal to 6 and less than or equal to 100. x is greater than or equal to 4 and less than or equal to 700; alternatively, x is greater than or equal to 10 and less than or equal to 500. x' is greater than or equal to 10 and less than or equal to 2250; alternatively, x' is greater than or equal to 75 and less than or equal to 1000. The drawing, Formula XXVI, represents the polymer as a block copolymer but it may have a more random topology. The synthesis is straightforward. Reacting a dihydroxy-PEG with two equivalents of cyclic lactone monomer yields the PEG-dilactide. This reaction proceeds via stannous-octanoate-catalyzed ring opening. The urethane polymer can be made by a two-step reaction in one pot. First, the PEG-dilactide can be reacted with the complete amount of 1,4-diisocyanatobutane. Once this has reacted, adding all of the 1,4-butanediamine would cause chain extension. Such a polymer could be called a poly(ester-urethane)urea.

In a poly(ester-urethane)urea polymer, a PEG is incorporated into the polymer backbone and attached at both ends, making it a block copolymer of PEG and poly(urethane)urea. The hard segment has urea linkages while the PEG soft segment has urethane and ester linkages. Polyurea hard segments are crystalline and hydrophobic. But the PEG content can make the polymer more hydrophilic and non-fouling. It also makes the polymer swell more in water and have a lower tensile strength. In some embodiments, this polymer will have a high PEG content while maintaining good mechanical properties. The soft segment will degrade preferentially. Having high-molecular weight hard segments composed of only the 1,4-diisocyanate and the diamino compound may be less preferred because these will eventually be released and degraded in a later timeframe. If desired, adjusting the stoichiometry and reaction conditions can limit the proportion of high-molecular-weight urea hard segments and the size of these segments.

degrade faster than the polymer depicted in Formula XXVI. The synthesis is straightforward. The caprolactide-derivatized PEG can form in a ring-opening reaction on caprolactone using PEG as the initiator. The urethane synthesis could be two-step where the soft segment is made first. Or it could be synthesized in one-step, but that tends to leave unreacted PEG-caprolactide.

Bioabsorbable Poly(ester-urethane) Urea with Pendant PEG Groups

In this polymer, the backbone can be a poly(ester-urethane) urea, and PEG can be present as pendant groups, which those of ordinary skill in the art believe makes PEG more available for coating-surface interactions because the PEG is tethered at only one end. Such pendant groups can either be attached after polymerization, such as through polymer-analogous transformation reactions, or be present during polymerization. Initially, having them present saves a reaction step. Depending on the PEG molecular weight, PEG end groups typically have a lower reactivity. A way around this is to use a monomethoxy-PEG where the other end is a primary amine group.

A monomethoxy-PEG can be incorporated into the polymer backbone with urea linkages. In this embodiment, PEG attaches via an amide linkage, so it usually only splits off upon enzymatic cleavage of the amide bond or cleavage of the backbone. Alternatively, using a diol generates ester linkages. One useful synthetic path would be as shown in Reaction Scheme I.

1,2-Diisocyanatoethane/PEG-caprolactide/1,4-butanediol

Formula XXVII

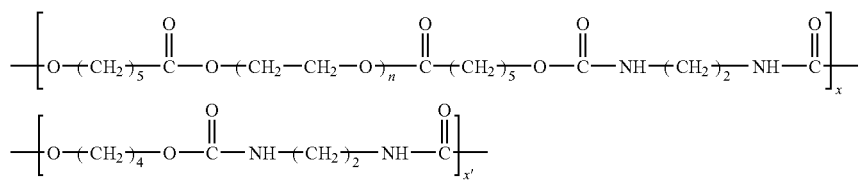

Reaction Scheme I

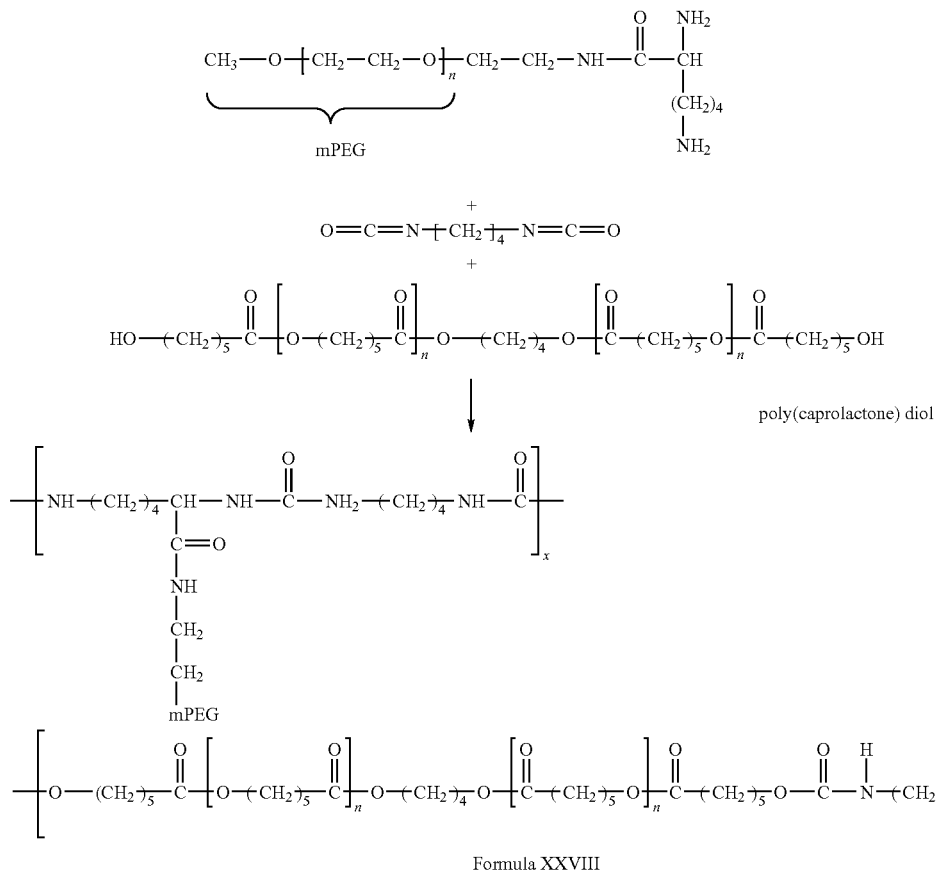

Formula XXVIII

In Formula XXVIII, n can be 0 to 40, and the central moiety in the caprolactone diol can be based on or a derivative of any $C_2$ to $C_{16}$ diol.

Poly(ester-urethane)-Hyaluronic Acid

Hyaluronic acid (HA) is a multifunctional molecule and, therefore, it is difficult to selectively incorporate into polymers. One approach is to first synthesize a polymer similar to that shown above in Formula XXVIII, except that a benzyl alcohol ester replaces the mPEG-amide group. This benzyl group can be selectively removed by hydrogenolysis after polymerization. The free carboxyl formed can then be coupled to an HA that has been derivatized by adipic dihydrazide. Alternatively, for Reaction Scheme II, below, a molar ratio of ethanol to 1,4-butanediisocyanate to caprolactonediol of 1:2:1 can be added to the reaction mixture. Control over the stoichiometry will yield the isocyanate-terminated polymer, Formula XXIX, which is then reacted with HA, as shown in Reaction Scheme II, below.

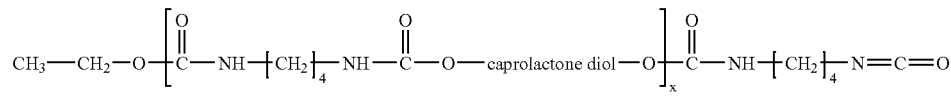

Formula XXIX

Reaction Scheme II

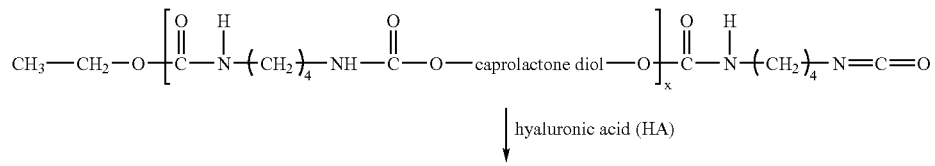

hyaluronic acid (HA)

-continued

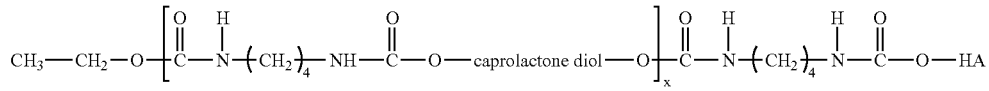

Formula XXX

In some embodiments of Formula XXX, x is greater than or equal to 1 and less than or equal to 1200; alternatively, x is greater than or equal to 3 and less than or equal to 500. In some embodiments, y is greater than or equal to 1 and less than or equal to 1667; alternatively, n is greater than or equal to 10 and less than or equal to 500. One of ordinary skill recognizes that two or more functional groups of HA can react to form the polymers shown in Formula XXX. These functional groups have the following identity: hydroxyl groups and carboxylic acid groups.

In addition to forming non-fouling coatings, these polymers, due to their tunable hydration properties, may also be used for the delivery or local delivery of proteins, peptides, and other biological molecules. These polymers may be coated onto bare metal stents or be coated on top of a drug eluting coating already present on the stent. Therapeutic agents may also be added to these bioabsorbable, non-fouling polymers making them bioabsorbable, drug eluting, coatings.

Various invention polymer or composition embodiments can be branched or can be cross-linked, partially cross-linked, or not cross-linked, as desired, as described above. Branching refers to pendant groups bonded to the polymer backbone. An example, without limitation, of a branched polymer is shown in Formula XXVIII. Cross-linking refers to the creation of covalent linkages between two or more polymer chains or two or more locations on a single polymer chain by reaction of separate multi-functional cross-linking agents with reactive functional groups appended to the polymer backbone or incorporated into the backbone.

In some instances, cross-linking occurs through functional groups pendant from the polymer backbone. For instance, in some embodiments urethanes or amides in the backbone can serve as the cross-linking site, such as via the use of diisocyanates. Those of ordinary skill in the art will recognize that other ways exist of achieving cross-links between polymer chains function with invention copolymers. For example, to UV crosslink the polymers, some embodiments may have UV-polymerizable groups in the monomers. Such groups are typically unsaturated diols, or pendant acrylates or methacrylates. One general scheme could include placing acrylate or methacrylate groups pendant onto, for example, an amino acid before the condensation polymerization. In another scheme, the acrylate or methacrylate groups would be present on the PEG based-amine, aliphatic diamine, or a difunctional phenyl moiety (e.g., 1,4-benzenedimethanol). This scheme is workable when condensation reactions are selective enough to leave the acrylate or methacrylate groups intact. This gives rise to another class of polymers.

Some embodiments comprise invention polymers or compositions coated onto a medical device containing or constructed from a polymer, a medical device containing or constructed from a metal, or a bare medical device, or invention polymers coated on top of a drug coating already present on a medical device. Alternatively, some embodiments comprise invention polymers or compositions disposed between a medical device and a drug coating. Also, some embodiments comprise invention polymers or compositions composing polymer-based medical devices or invention polymers or compositions composing medical device substrates (implantable or not). Some invention embodiments comprise medical devices not made from polymer-containing or -constructed stents. Some invention embodiments comprise stents not made from metal-containing or constructed stents.

In some embodiments, invention polymers or compositions serve as the base material for coatings on medical devices. In some embodiments, coatings may contain a primer layer composed of an invention polymer or composition or composed of a type-two polymer, as described below. Some embodiments exclude a primer layer.

Some embodiments add conventional drugs, such as small, hydrophobic drugs, to invention polymers or compositions (as discussed in any of the embodiments, above), making them biodegradable, drug systems. Some embodiments graft on conventional drugs or mix conventional drugs with invention polymers or compositions. Invention polymers or compositions can be coated as blends with a variety of biobeneficial polymers. Moreover, they can serve as base or topcoat layers for biobeneficial polymer layers.

The bioactive agents can be any molecule or moiety capable of contributing to a therapeutic effect, a prophylactic effect, both a therapeutic and prophylactic effect, or other biologically active effect in a mammal. The agent can also have diagnostic properties. The bioactive agents include, for example, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, for example, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, functional derivatives, structural derivatives, salts or combinations thereof. It is to be appreciated that one skilled in the art should recognize that any of these groups, subgroups, and individual bioactive, agents may be specifically excluded from some embodiments of the present invention.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic, or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.) and any prodrugs, metabolites, analogs, homologues, congeners, functional derivatives, structural derivatives, salts, or combinations thereof.

Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, adriamycin, mutamycin, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, functional derivatives, structural derivatives, salts or combinations thereof.

Antiplatelets, anticoagulants, antifibrin, and antithrombins include, for example, aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/IIIa platelet membrane receptor antagonist antibody, recombinant hirudin, and thrombin inhibitors (ANGIOMAX®, Biogen, Inc.), and any prodrugs, metabolites, analogs, homologues, congeners, functional derivatives, structural derivatives, salts or combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, functional derivatives, structural derivatives, salts or combinations thereof.

Antiallergic agents include, for example, pemirolast potassium (ALAMAST®, Santen, Inc.), and any prodrugs, metabolites, analogs, homologues, congeners, functional derivatives, structural derivatives, salts or combinations thereof.

Examples of anti-inflammatory agents including steroidal and non-steroidal anti-inflammatory agents such as tacrolimus, dexamethasone, clobetasol, and any prodrugs, metabolites, analogs, homologues, congeners, functional derivatives, structural derivatives, salts or combinations thereof.

Other bioactive agents useful in the present invention include, for example, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and any prodrugs, metabolites, analogs, homologues, congeners, functional derivatives, structural derivatives, salts or combinations thereof.

Free radical scavengers include, for example, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, functional derivatives, structural derivatives, salts or combinations thereof.

Nitric oxide donors include, for example, S-nitrosothiols, nitrites, N-oxo-N-nitrosamines, substrates of nitric oxide synthase, diazenium diolates such as spermine diazenium diolate and any analogs, homologues, congeners, functional derivatives, structural derivatives, salts or combinations thereof.

Other therapeutic substances or agents that may be appropriate include imatinib mesylate, pimecrolimus, and midostaurin.

Other therapeutic substances or agents which may be appropriate include alpha-interferon, bioactive RGD, and genetically engineered epithelial cells.

The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of diagnostic agents include radio opaque materials and include, for example, materials comprising iodine or iodine-derivatives such as, for example, iohexyl and iopamidol, which are detectable by x-rays. Other diagnostic agents such as, for example, radioisotopes; are detectable by tracing radioactive emissions. Other diagnostic agents may include those that are detectable by magnetic resonance imaging (MRI), ultrasound and other imaging procedures such as, for example, fluorescence and positron emission tomography (PET). Examples of agents detectable by MRI are paramagnetic agents, which include, for example, gadolinium chelated compounds. Examples of agents detectable by ultrasound include, for example, perflexane. Examples of fluorescence agents include, for example, indocyanine green. Examples of agents used in diagnostic PET include, for example, fluorodeoxyglucose, sodium fluoride, methionine, choline, deoxyglucose, butanol, raclopride, spiperone, bromospiperone, carfentanil, and flumazenil.

Some embodiments choose the drug such that it does not contain at least one of or any combination of antiproliferative, antineoplastic, antiinflammatory, antiplatelet, anticoagulant, antifibrin, antithrombin, antimitotic, antibiotic, or antioxidant substances. Some invention embodiments choose the drug such that it does not contain at least one of or any combination of actinomycin D, derivatives and analogs of Actinomycin D, dactinomycin, actinomycin IV, actinomycin $I_1$, actinomycin $X_1$, actinomycin $C_1$, paclitaxel, docetaxel, aspirin, sodium heparin, low molecular weight heparin, hirudin, argatroban, forskolin, vapiprost, prostacyclin, prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor and 7E-3B, methotrexate, azathioprine, vincristine, vinblastine, fluorouracil, adriamycin, mutamycin, angiopeptin, angiotensin converting enzyme inhibitors, CAPTOPRIL, CILAZAPRIL, or LISINOPRIL, calcium channel blockers, Nifedipine, colchicine, fibroblast growth factor (FGF) antagonists, histamine antagonist, LOVASTATIN, monoclonal antibodies, PDGF receptors, nitroprusside, phosphodiesterase inhibitors, prostaglandin inhibitor, Seramin, PDGF antagonists, serotonin blockers, thioprotease inhibitors, triazolopyrimidine, nitric oxide, alpha-interferon, genetically engineered epithelial cells, dexamethasone, estradiol, clobetasol propionate, cisplatin, insulin sensitizers, receptor tyrosine kinase inhibitors, carboplatin, rapamycin, 40-O-(2-hydroxy)ethyl-rapamycin, or a functional analogs of 40-O-(2-hydroxy)ethyl-rapamycin, structural derivative of 40-O-(2-hydroxy)ethyl-rapamycin, 40-O-(3-hydroxy)propyl-rapamycin, and 40-O-2-(2-hydroxy)ethoxyethyl-rapamycin.

Some invention embodiments comprise a drug or drug combination, and some require a drug or combination of drugs. Of the drugs specifically listed above, some invention embodiments exclude a single or any combination of these drugs.

Some invention embodiments comprise blends of invention polymers or, compositions, as described above, with another polymer or polymers. For convenience, the invention polymers or compositions described above are referred to as type-one polymers and the other polymer or polymers are referred to as type-two polymers. Preferably, the polymers blended with the invention polymers or compositions would be biodegradable. However, they may also be durable as the blend can have other useful properties. As the invention polymers or compositions span a range of polarities and solubility parameters, the range of type two polymers that can be miscible is also large. Furthermore, microstructural phase separation, as occurs in ABS for example, of the invention polymer or composition and a type two polymer can also be desired in some instances as it can lead to useful mechanical properties. These blends could also be formulated to modulate or tune the release rate of drugs from coatings, reservoirs, or particles composed of these blends and drugs or therapeutic agents. Blends with other polymers can be formulated to modulate the mechanical properties of invention polymers or compositions. For instance, type-two polymers could be blended into invention polymers or compositions to modify mechanical or biological properties or vice versa. Type-two polymers could also be blended into invention polymers or compositions to modify degradation rates.

Type-two polymers include, among others, polycaprolactone, poly(D,L-lactide), poly(L-lactide), poly(D,L-lactide-co-L-lactide), poly(lactic acid), poly(glycolide), poly(D,L-lactide-co-glycolide), poly(dioxanone), poly(4-hydroxybutyrate), poly(3-hydroxybutyrate), poly(3-hydroxy valerate), poly(3-hydroxybutyrate-co-3-hydroxyvalerate), poly(tyrosine derived carbonates), poly(tyrosine arylates), poly(imino carbonates), poly(trimethylene carbonate), poly(anhydrides), poly(orthoesters), and poly(ester amides) or combinations of these polymers. In some embodiments, polymer blends with invention polymers or compositions do not contain at least one of polycaprolactone, poly(D,L-lactide), poly(L-lactide), poly(D,L-lactide-co-L-lactide), poly(glycolide), poly(D,L-lactide-co-glycolide), poly(lactic acid), poly(dioxanone), poly(4-hydroxybutyrate), poly(3-hydroxybutyrate), poly(3-hydroxy valerate), poly(hydroxybutyrate-co-hydroxyvalerate), poly(tyrosine derived carbonates), poly(tyrosine arylates), poly(imino carbonates), poly(trimethylene carbonate), poly(anhydrides), poly(orthoesters), or poly(ester amides).

Type-two polymers also include ethylene vinyl alcohol copolymer, poly(hydroxyvalerate); poly(L-lactic acid); polycaprolactone; poly(L-lactide-co-caprolactone); poly(D,L-lactide-co-caprolactone); poly(L-lactide-co-glycolide); poly(D,L-lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin; fibrinogen, cellulose, starch, collagen and hyaluronic acid; poly(ester-urethanes); poly(ether-urethanes); poly(urea-urethanes); poly(silicone-urethanes); polyurethanes; silicones; polyesters; styrene-ethylene/butylene-styrene triblock copolymers; styrene-isobutylene-styrene triblock copolymers; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; poly(vinylidene fluoride-co-hexafluoropropene), poly(vinylidene fluoride-co-chlorotrifluoropropene); poly(vinyl fluoride); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, poly(butyl methacrylates), poly(alkoxy acrylates), poly(alkoxy methacrylates); acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; methyl cellulose; ethyl cellulose; cellulose ethers; hydroxyethyl cellulose; hydroxypropyl cellulose; and carboxymethyl cellulose.

In some embodiments, polymer blends with invention polymers or compositions do not contain at least one of ethylene vinyl alcohol copolymer, poly(hydroxyvalerate); poly(L-lactic acid); polycaprolactone; poly(L-lactide-co-caprolactone); poly(D,L-lactide-co-caprolactone); poly(L-lactide-co-glycolide); poly(D,L-lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; poly(ester-urethanes); poly(ether-urethanes); poly(urea-urethanes); poly(silicone-urethanes); polyurethanes; silicones; polyesters; styrene-ethylene/butylene-styrene triblock copolymers; styreneisobutylene-styrene triblock copolymers; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; poly (vinylidene fluoride-co-hexafluoropropene), poly(vinylidene fluoride-co-chlorotrifluoropropene); poly(vinyl fluoride); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, poly(butyl methacrylates), poly(alkoxy acrylates), poly (alkoxy methacrylates); acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; methyl cellulose; ethyl cellulose; cellulose ethers; hydroxyethyl cellulose; hydroxypropyl cellulose; and carboxymethyl cellulose.

Some invention embodiments comprise, and some invention embodiments require, a type-two polymer used along with invention polymers or compositions. Some invention embodiments comprise and some invention embodiments require combining at least two type-two polymers with invention polymers or compositions. Of the type-two polymers disclosed above, some invention embodiments exclude any of or any combination of type-two polymers.

In some embodiments, the invention polymers or compositions are mixed or blended with the type-two polymers. For example, some embodiments comprise invention polymers or compositions physically blended with PEG, POLYACTIVE, or other biobeneficial polymers. Additionally, some embodiments employ invention polymers or compositions blended with biobeneficial polymers and type-two polymers.

Some embodiments comprise invention polymers or compositions combined with other polymers in multilayer arrangements. For example, an invention polymer or composition could under- or over-lay another polymer such as a polymer coated on a device, a medical device, an implantable medical device, or a stent. The invention polymer or composition can be used neat in this regard, or it can first be mixed with a separate invention polymer or composition or a type-two polymer before layering. In some embodiments, invention polymers or compositions do not underlay another polymer; in other embodiments, invention polymers or compositions must overlay another polymer.

Examples of implantable devices useful in the present invention include self-expandable stents, balloon-expandable stents, stent-grafts, grafts (e.g., aortic grafts), vascular grafts, artificial heart valves, closure devices for patent foramen ovale, cerebrospinal fluid shunts, pacemaker electrodes, guidewires, ventricular assist devices, artificial hearts, cardiopulmonary by-pass circuits, blood oxygenators, and endocardial leads (e.g., FINELINE and ENDOTAK, available from Guidant Corporation, Santa Clara, Calif.). The underlying structure of the device can be of virtually any design. The device can comprise a metallic material or an alloy such as, but not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Some invention embodiments define the genera of medical devices to exclude at least one of self-expandable stents, balloon-expandable stents, stent-grafts, grafts (e.g., aortic grafts), vascular grafts, artificial heart valves, cerebrospinal fluid shunts, pacemaker electrodes, guidewires, ventricular assist devices, artificial hearts, cardiopulmonary by-pass circuits, blood oxygenators, or endocardial leads.

A coating for an implantable medical device, such as a stent; according to embodiments of the present invention, can be a multi-layer structure that can include any one of or any combination of the following three layers:

a primer layer;

a drug-polymer layer (also referred to as "reservoir" or "reservoir layer") or alternatively a polymer-free drug layer; and/or a topcoat layer, which is likewise drug containing or drug free.

In some embodiments, forming each medical device coating layer comprises dissolving the polymer or a polymer blend in a solvent or a solvent mixture, and applying the solution onto the medical device (such as by spraying the medical device with the solution or by dipping the medical device into the solution). After applying the solution onto the medical device, the coating dries by solvent evaporation. Drying at elevated temperatures accelerates the process.

Combining the drug with the polymer solution, as described above, provides for incorporating the drug into the reservoir layer. Alternatively, dissolving the drug in a suitable solvent or solvent mixture and applying the drug solution to the medical device provides for a substantially polymer-free drug layer.

Instead of introducing the drug as a solution, some embodiments introduce the drug as a colloid, such as a suspension in a solvent. Dispersing the drug in the solvent uses conventional techniques. Depending on a variety of factors, e.g., the nature of the drug, those having ordinary skill in the art can select the solvent for the suspension, as well as the quantity of the dispersed drug. Some embodiments mix these suspensions with a polymer solution and apply the mixture onto the device, as described above. Alternatively, some embodiments apply the drug suspension to the device without mixing it with the polymer solution.

The drug-polymer layer can be applied directly onto at least a part of the medical device surface to serve as a reservoir for at least one active agent or a drug. The optional primer layer can interleave between the device and the reservoir to improve polymer adhesion to the medical device. Some embodiments apply the topcoat layer over at least a portion of the reservoir layer, and the topcoat layer serves as a rate limiting membrane that helps to control the rate of release of the drug.

Some drug releasing processes include at least two steps. First, the topcoat polymer absorbs the drug at the drug-polymer-topcoat interface. Next, the drug diffuses through the topcoat using empty spaces between the polymer molecules as diffusion pathways. Next, the drug arrives to the outer surface of the topcoat, and desorbs into the blood stream.

Some invention embodiments can be described as a composition comprising the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable.

Some invention embodiments can be described as a composition represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable.

Some invention embodiments can be described as a medical device or medical device coating comprising at least one type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable.

Some invention embodiments can be described as a medical device or medical device coating comprising at least two type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, in which the first type-one polymer is disposed on the surface of the device to form a polymer layer and another type-one polymer is disposed on the polymer layer.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, in which the first type-one polymer is disposed on the surface of the device to form a polymer layer and another type-one polymer is disposed on the polymer layer.

Some invention embodiments can be described as a medical device or medical device coating comprising at least one type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers.

Some invention embodiments can be described as a medical device or medical device coating comprising at least one type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

Some invention embodiments can be described as a medical device or medical device coating comprising at least one type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene (carbonate), poly(anhydrides), poly(orthoesters), poly(ester amides) or their mixtures. In some of these embodiments, the type-one polymer is disposed on the surface of the device to form a polymer layer and another type-one polymer is disposed on the polymer layer.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. In some of these embodiments, the type-one polymer is disposed on the surface of the device to form a polymer layer and another type-one polymer is disposed on the polymer layer.

Some invention embodiments can be described as a medical device or medical device coating comprising at least one type-one polymer, wherein type-one polymers are the polymerization product of an A-moiety derived from a diisocyanate; a B-moiety derived from a chain extender; and a C-moiety derived from a biobeneficial moiety, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. In some of these embodiments, the type-one polymer is disposed on the surface of the device to form a polymer layer and another type-one polymer is disposed on the polymer layer.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and at least one type-two polymer in which type-two polymers are biocompatible polymers selected from polycaprolactone, poly(D,L-lactide); poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. In some of these embodiments, the type-one polymer is disposed on the surface of the device to form a polymer layer and another type-one polymer is disposed on the polymer layer.

Some invention embodiments can be described as a composition comprising the polymerization product of an A-moiety derived from a diisocyanate compound with a formula $$O{=}C{=}N-Q_1-N{=}C{=}O;$$

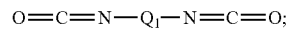

a B-moiety derived from a chain extender, which is a compound with a formula $W_2\text{-}Q_2\text{-}W_1$; and a C-moiety derived from a biobeneficial moiety, which is a compound with a formula A1-BB-A2, wherein Q1 and Q2 independently represent 1-50 carbon atom moieties, W1 and W2 independently represent O-, S-, or N-containing groups, A1 and A2 independently represent 1-20 carbon-atom hydroxy acids, hydroxy acid oligomers, amino acid, or amino acid oligomers, and BB represents a biobeneficial moiety.

Some invention embodiments can be described as a medical device or medical device coating comprising at least one type-one polymer composition comprising the polymerization product of an A-moiety derived from a diisocyanate compound with a formula $$O{=}C{=}N-Q_1-N{=}C{=}O;$$

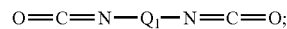

a B-moiety derived from a chain extender, which is a compound with a formula $W_2\text{-}Q_2\text{-}W_1$; and a C-moiety derived from a biobeneficial moiety, which is a compound with a formula A1-BB-A2, wherein Q1 and Q2 independently represent 1-50 carbon atom moieties, W1 and W2 independently represent O-, S-, or N-containing groups, A1 and A2 independently represent 1-20 carbon-atom hydroxy acids, hydroxy acid oligomers, amino acid, or amino acid oligomers, and BB represents a biobeneficial moiety.

Some invention embodiments can be described as a medical device or medical device coating comprising at least one type-one polymer composition comprising the polymerization product of an A-moiety derived from a diisocyanate compound with a formula

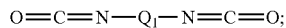

$$O=C=N-Q_1-N=C=O;$$

a B-moiety derived from a chain extender, which is a compound with a formula $W_2-Q_2-W_1$; and a C-moiety derived from a biobeneficial moiety, which is a compound with a formula A1-BB-A2, wherein Q1 and Q2 independently represent 1-50 carbon atom moieties, W1 and W2 independently represent O-, S-, or N-containing groups, A1 and A2 independently represent 1-20 carbon-atom hydroxy acids, hydroxy acid oligomers, amino acid, or amino acid oligomers, and BB represents a biobeneficial moiety, and further comprising a type-two polymer, wherein type-two polymers are biocompatible and are selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

Some invention embodiments can be described as a medical device or medical device coating comprising at least one type-one polymer composition comprising the polymerization product of an A-moiety derived from a diisocyanate compound with a formula

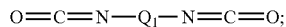

$$O=C=N-Q_1-N=C=O;$$

a B-moiety derived from a chain extender, which is a compound with a formula $W_2-Q_2-W_1$; and a C-moiety derived from a biobeneficial moiety, which is a compound with a formula A1-BB-A2, wherein Q1 and Q2 independently represent 1-50 carbon atom moieties, W1 and W2 independently represent O-, S-, or N-containing groups, A1 and A2 independently represent 1-20 carbon-atom hydroxy acids, hydroxy acid oligomers, amino acid, or amino acid oligomers, and BB represents a biobeneficial moiety, and further comprising a type-two polymer, wherein type-two polymers are biocompatible and are selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. In some of these embodiments, the medical device or medical device coating comprises at least one inner layer and one outer layer wherein the inner layer is a type-two polymer and the outer layer is a type-one polymer; or the inner layer is a type-one polymer and the outer layer is a type-two polymer.

Some invention embodiments can be described as a medical device or a medical device coating comprising at least one type-one polymer, wherein type-one polymers can be represented by one of Formula I-Formula VII, in which the biobeneficial moiety is connected to a hydroxyacid, a hydroxyacid composition, a hydroxyacid oligomer, an amino acid, an amino acid composition, or an amino acid oligomer and in which the hydroxyacid composition, the hydroxyacid oligomer, the amino acid, the amino acid composition, or the amino acid oligomers is bioabsorbable, and further comprising a type-two polymer, wherein type-two polymers are biocompatible and are selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures. In some of these embodiments, the medical device or medical device coating comprises at least one inner layer and one outer layer wherein the inner layer is a type-two polymer and the outer layer is a type-one polymer; or the inner layer is a type-one polymer and the outer layer is a type-two polymer.

In some of these embodiments, the method can be described as reacting an amount of hydroxy-acid- or amino-acid-modified biobeneficial composition with an amount of diisocyanate to yield a first intermediate; polymerizing the type-two polymer precursor to yield a second intermediate; and reacting the first intermediate, the second intermediate, and a chain extender.

In some embodiments, any of the compositions described above can be made with a method that can be described as reacting an amount of hydroxy-acid- or amino-acid-modified biobeneficial composition with an amount of diisocyanate to yield a first intermediate; polymerizing the type-two polymer precursor to yield a second intermediate; and reacting the first intermediate, the second intermediate, and a chain extender.

In some embodiments of the methods described above the amount of hydroxy-acid- or amino-acid-modified biobeneficial composition ranges from 0.1 mole % to 10 mole % of the amount of diisocyanate or ranges from 0.1 weight % to 10 weight % of the amount of diisocyanate.

In some of the embodiments of the methods described above, the amount of hydroxy-acid- or amino-acid-modified biobeneficial composition ranges from 0.33 mole % to 3 mole % of the amount of diisocyanate or ranges from 0.33 weight % to 3 weight % of the amount of diisocyanate.

EXAMPLES

Prophetic Example 1

Synthesis of co-poly-{[PEG300-bis-(D,L-lactide)-1, 4-butane carbamate]$_{0.80}$-[1,4-butanediamine-1,4-butane diureab]$_{0.20}$}.

Synthesis of PEG300-bis-(D,L-lactide): To a 1000 ml, 3 necked flask, equipped with vacuum line, argon purge, mechanical stirrer and oil bath is added poly(ethylene glycol), MW=300 (200 gm, 0.667 mole), and D,L-lactide (192 gm, 1.33 mole). Vacuum is applied and the mixture is heated to 110° C. with stirring for about one hour. After purging with argon, tin (II) 2-ethylhexanoate (5.39 gm, 0.0133 moles) is added and the solution heated at 110° C. with stirring for about 2 hours. While still molten, the reaction mixture is added to 2 liters of a 50/50 (w/w) blend of diethyl ether and hexane with stirring. After isolation by filtration, the polymer is dried at 40° C. at a vacuum of about 1 Torr for 24 hours.

To a 500 ml, 3-necked flask equipped with argon purge, mechanical stirrer, an oil bath is added PEG300-bis-(D,L-lactide) (117.2 gm, 0.2 mole), 1,4-diisocyanatobutane (35 gm, 0.25 mole), anhydrous triethylamine (0.253 gm, 0.0025 mole), and anhydrous dimethylformamide (150 ml). While under argon purge, the reaction mixture is heated at 80° C. with stirring for about 2 hours. 1,4-butanediamine (4.4 gm, 0.05 moles) is then added, and the reaction mixture is stirred at 80° C. for about another four hours. After cooling, the reaction mixture is poured into 1 liter of 50/50 (w/w) blend of ethyl acetate and hexane. After isolation by filtration, the polymer is dried at 40° C. under a vacuum of about 1 Torr for about 48 hours. This results in a biodegradable poly(ether ester urea urethane) containing about 38% PEG300 by weight.

Prophetic Example 2

Synthesis of co-poly-{[PEG600-bis-(L-leucine)-N, N'-L-lysine ethyl ester urea]$_{0.80}$-[1,4-oxybutane-N, N'-L-lysine ethyl ester carbamate)]$_{0.20}$}

Synthesis of PEG600-bis-(L-leucine): To a 2000 ml, 3-necked, flask equipped with argon purge, mechanical stirrer, thermometer, addition port, reflux condenser with Dean-Stark trap, and oil bath is added poly(ethylene glycol) MW=600 (100 gm, 0.167 mole), L-leucine (45.92 gm, 0.35 mole), p-toluenesulfonic acid monohydrate (69.8 gm, 0.367 mole), and benzene (750 ml). While under argon, the reaction mixture is heated to reflux with a heating rate to generate about 2 drops/second reflux. After the stoichiometric amount of water has been isolated (12.6 gm, 0.7 moles), the reaction is cooled, and 750 ml of hexane is added. After stirring for 30 minutes, the product is isolated by filtration and dried under vacuum at 40° C. overnight. The product is combined with 500 ml of diethyl ether saturated with water, stirred for 10 minutes, and the product isolated by suction filtration. The process is repeated with 500 ml of anhydrous ether and after isolation, the product is dried at 40° C. at a vacuum of about 1 Torr for about 48 hours.

To a 500 ml, 3-necked, reaction flask equipped with mechanical stirrer, argon purge, vacuum line, and oil bath is added PEG600-bis-L-leucine ditosylate (234 gm, 0.2 mole), anhydrous 1,4-butanediol (4.51 gm, 0.05 mole), anhydrous triethylamine (20.24 gm, 2.2 mole) and anhydrous dimethylformamide (250 ml). After dissolution, L-lysine ethyl ester diisocyanate (56.5 gm, 0.25 moles) is added and the reaction heated under argon at 80° C. with stirring for 6 hours. After cooling, the reaction mixture is poured into 2 liters of cold deionized water with stirring, the polymer isolated by filtration, and the process repeated. The polymer is dissolved in 500 ml of chloroform and filtered through a dry disc apparatus (Horizon Technologies, Atkinson, N.H.) to remove particulates and water. After removing most of the chloroform by rotary evaporation, the solution is placed into Teflon pans and dried at 40° C. under a vacuum of about 1 Torr for about 48 hours. This results in a biodegradable poly(ether ester urea urethane) containing about 53% PEG600 by weight.

Prophetic Example 3

Synthesis of co-poly-{[poly(caprolactone)-1,4-butane dicarbamate]$_{0.325}$-[N,N'-L-lysine mPEG amide-1,4-butane diurea]$_{0.675}$}, Formula XXVIII Synthesis of L-lysine mPEG amide dihydrochloride. To a 250 ml, 3-necked flask equipped with magnetic stir bar and argon purge is added N,N'-t-BOC-L-lysine (10 gm, 0.0289 mole), methoxypoly(ethylene glycol) (mPEG-amine MW=560) (Quanta Biodesign, Powell Ohio) (16.18 gm, 0.0289 mole), and chloroform (125 ml). After dissolution, dicyclohexylcarbodiimide (6.27 gm, 0.0304 moles) is added and the solution stirred at ambient temperature overnight. After filtration to remove the dicyclohexylurea, the chloroform solution is dried over magnesium sulfate, and the chloroform removed by rotary evaporation. The residue is dissolved in 125 ml of methanol, acetyl chloride (29.4 gm, 0.375 moles) is added, and the solution is stirred at ambient temperature for 30 minutes. It is poured into 250 ml of deionized water, and the aqueous phase extracted with three, 100 ml portions of methylene chloride. The organic extracts are combined, the solvent removed by rotary evaporation and the residue dried at 40° C. under a vacuum of about 1 Torr for about 48 hours.

To a 100 ml, 3-necked flask, equipped with magnetic stirrer, argon purge, vacuum line, and oil bath is added anhydrous poly(caprolactone) diol (MW=550, Solvay) (4.73 gm, 0.0086 mole), 1,4-butanediisocyanate (3.71 gm, 0.0265 mole), and dimethylformamide (25 ml). In an argon atmosphere, the solution is heated with stirring at 80° C. for two hours. Triethylamine (3.61 gm, 0.0357 moles) and L-lysine mPEG amide dihydrochloride (13.6 gm, 0.0179 moles) are added and the solution stirred at 80° C. for another two hours. After cooling to room temperature, the reaction mixture is poured into 250 ml of diethylether to precipitate the polymer. The polymer is redissolved in methanol (100 ml) and precipitated again in 500 ml of diethylether after which it is dried at 40° C. under a vacuum of 1 Torr for about 24 hours. This results in a biodegradable poly(ester urea urethane) with grafted mPEG and containing about 50% mPEG560 by weight.

Prophetic Example 4

Coating a Stent with the Composition of Example 1

A composition can be prepared by mixing the following components:
about 2.0% (w/w) of poly(D,L-lactide);
about 0.2% (w/w) of paclitaxel; and
the balance a 50/50 (w/w) blend of chloroform and 1,1,2-trichloroethane.

The composition can be applied onto the surface of bare 12 mm small VISION™ stent (Guidant Corp.). The coating can be sprayed and dried to form a drug reservoir layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied at per one spray pass. About 180 μg of wet coating can be applied, and the stent can be dried for about 10 seconds in a flowing air stream at about 50° C. between the spray passes. The stents can be baked at about 50° C. for about one hour, yielding a drug reservoir layer composed of approximately 150 μg of the polymer of Example 1 and about 14 μg of paclitaxel.

A second composition can be prepared by mixing the following components:

about 2.0% (w/w) of the polymer of example 1;

the balance a 50/50 (w/w) blend of acetone and dimethylformamide.

The second composition can be applied onto the dried drug reservoir layer to form a biobeneficial topcoat layer using the same spraying technique and equipment used for applying the reservoir. About 120 μg of wet coating can be applied followed by drying and baking at about 50° C. for about 2 hours, yielding a dry topcoat layer having solids content of about 100 μg.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects (such as monomer type) composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists in which that aspect specifically excludes that aspect.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically include the value or the conditions for the aspect.

The invention claimed is:

1. A composition comprising:
    an A-moiety derived from a diisocyanate;
    a B-moiety derived from a chain extender; and
    a C-moiety derived from a biobeneficial moiety selected from the group consisting of poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), phosphoryl choline, heparin, chondroitin sulfate, glycosaminoglycans, chitosan, polyethylene oxide, or any combination of these; wherein:
    the composition comprises one of the following formulas:

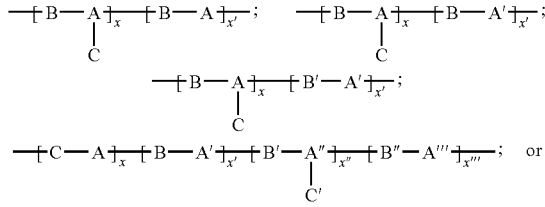

-continued

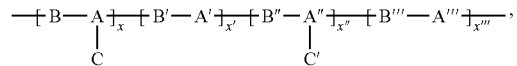

wherein x, x', x", and x''' are integers from 1-50,000; A, A', A", and A''' independently represent A-moieties; B, B', B", and B''' independently represent B-moieties; and C and C' independently represent C-moieties.

2. The composition of claim 1 wherein diisocyanate(s) are selected such that at least one hydrolysis product of the diisocyanate(s) is a biocompatible diamine.

3. The composition of claim 1 wherein the diisocyanate is an aliphatic diisocyanate.

4. The composition of claim 3 wherein the diisocyanate is 1,4-diisocyanatobutane, 1,2-diisocyanatoethane, lysine ester diisocyanate, 1,5-diisocyanatopentane, or any combination of these.

5. The composition of claim 1 wherein the chain extender is biocompatible.

6. The composition of claim 1 wherein the biobeneficial moiety is connected to a hydroxyacid, a hydroxyacid composition, a hydroxyacid oligomer, an amino acid, an amino acid composition, or an amino acid oligomer.

7. The composition of claim 5 wherein the chain extender comprises an alcohol-amine, a diamine, a diol, a dithiol, or any combination of these.

8. The composition of claim 7 wherein
    the diamine is selected from 1,4-butanediamine, lysine ester, 1,2-ethanediamine, arginine ethyl ester, 1,5-pentanediamine, or any combination of these; or
    the diol is selected from 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, poly(caprolactone) diol, or any combination of these.

9. The composition of claim 1 wherein:
    the A-moiety is derived from a compound with a formula $$O=C=N-Q_1-N=C=O;$$

the B-moiety is derived from a compound with a formula

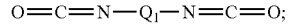

the C-moiety is derived from a compound with a formula

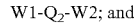

wherein
    Q1 and Q2 independently represent 1-50 carbon atom moieties;
    W1 and W2 independently represent O-, S-, or N-containing groups;
    A1 and A2 independently represent 1-20 carbon-atom hydroxy acids, hydroxy acid oligomers, amino acid, or amino acid oligomers; and
    BB represents a biobeneficial moiety.

10. The composition of claim 9 wherein Q1 and Q2 independently represent 1-20 carbon atom moieties.

11. The composition of claim 9 wherein W1 and W2 independently represent —OH or —NH$_2$.

12. The composition of claim 9 wherein A1 and A2 independently represent bioabsorbable hydroxy-acid radicals, a metabolic precursor to bioabsorbable hydroxy-acid radicals, bioabsorbable amino acid radicals, or a metabolic precursor to bioabsorbable amino acid radicals.

13. The composition of claim 10 wherein
the hydroxyacid is selected from 2-hydroxyacids, 3-hydroxy acids, 4-hydroxy acids, or ε-hydroxy-caproic acid, oligomers of the above, or any combination of these; or
the amino acid is glycine, valine, leucine, isoleucine, proline, phenylalanine, oligomers of the above, or any combination of these.

14. The composition of claim 9 wherein the biobeneficial moiety is poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), phosphoryl choline, heparin, chondroitin sulfate, glycosaminoglycans, chitosan, polyethylene oxide, or any combination of these.

15. The composition of claim 1 of the following formula:

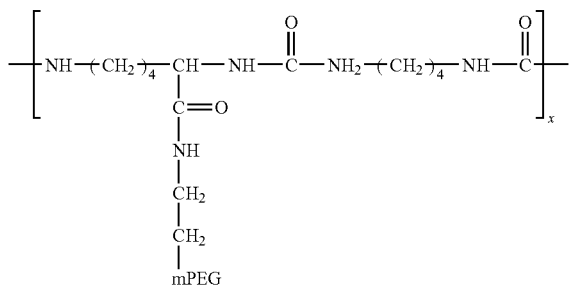

wherein
x is an integer greater than or equal to 1; and
mPEG represents a methoxy-poly(ethylene glycol) moiety.

16. A composition comprising a polymer comprising:
an A-moiety derived from a diisocyanate, wherein the diisocyanate is 1,4-diisocyanatobutane, 1,2-diisocyanatoethane, lysine ester diisocyanate, 1,5-diisocyanatopentane, or any combination of these;
a B-moiety derived from a chain extender comprising an alcohol-amine, diamine, diol or any combination of these wherein the diamine or diol is 1,4-butanediamine, Lysine Ester, 1,2-ethanediamine, Arginine Ethyl Ester, 1,5-pentanediamine, 1,3-propanediol, 1,2-propanediol, 1,4-butanediol, 1,6-hexanediol, 1,10-decanediol, cyclohexanedimethanol, and poly(caprolactone)diol, 1,5-pentanediol, 1,4-cyclohexanediol, 1,7-heptanediol, 1,8-octanediol, 1,9-nonanediol, 1,12-dodecanediol, caprolactone diol, or any combination of these; and
a C-moiety derived from a biobeneficial moiety wherein at least one C-moiety is appended from an A moiety as a side chain, the C-moiety comprising:
poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly(styrene sulfonate), poly(3-hydroxypropyl methacrylate), poly(3-hydroxypropyl methacrylamide), poly(alkoxy methacrylates), poly(alkoxy acrylates), polyarginine peptides (PAP), phosphoryl choline, heparin, chondroitin sulfate, glycosaminoglycans, chitosan, polyethylene oxide, or any combination of these, and
a hydroxyacid selected from 2-hydroxyacids, 3-hydroxy acids, 4-hydroxy acids, or ε-hydroxy-caproic acid, oligomers of the above, or any combination of these; or the amino acid is glycine, valine, leucine, isoleucine, proline, phenylalanine, oligomers of the above, or any combination of these,
wherein the biobeneficial moiety has a maximum molecular weight of 40,000±4,000 Daltons.

17. A medical device comprising at least one type-one polymer, wherein type-one polymers are the compositions of claim 1.

18. A medical device comprising at least one type-one polymer, wherein type-one polymers are the compositions of claim 9.

19. The medical device of claim 17 wherein the type-one polymer is coated onto the surface of the device to form a layer of polymer.

20. The medical device of claim 17 further comprising another type-one polymer, wherein the type-one polymer is disposed on the surface of the device to form a polymer layer and another type-one polymer is disposed on the polymer layer.

21. The medical device of claim 17 further comprising a type-two polymer, wherein type-two polymers are biocompatible and are selected from polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

22. The medical device of claim 21 comprising at least one inner layer and one outer layer wherein
the inner layer is a type-two polymer and the outer layer is a type-one polymer; or
the inner layer is a type-one polymer and the outer layer is a type-two polymer.

23. The medical device of claim 17 further comprising at least one therapeutic agent.

24. The medical device of claim 23 wherein the therapeutic agent is selected from proteins, peptides, antiproliferatives, antineoplastics, antiinflammatories, antiplateletes, anticoagulants, antifibrins, antithrombins, antimitotics, antibiotics, antioxidants, or their mixtures.

25. A method of preparing the composition of claim 1 comprising:
reacting an amount of hydroxy-acid- or amino-acid-modified biobeneficial composition with an amount of diisocyanate to yield an intermediate; and
reacting the intermediate with a chain extender.

26. The method of claim 25 wherein the amount of hydroxy-acid- or amino-acid-modified biobeneficial composition ranges from 0.1 mole % to 100 mole % of the amount of diisocyanate or ranges from 0.1 weight % to 100 weight % of the amount of diisocyanate.

27. The method of claim 26 wherein the amount of hydroxy-acid- or amino-acid-modified biobeneficial composition ranges from 0.33 mole % to 3 mole % of the amount of diisocyanate or ranges from 0.33 weight % to 3 weight % of the amount of diisocyanate.

28. The method of claim 25 wherein the diisocyanate is selected such that the hydrolysis product of the diisocyanate is a biocompatible diamine.

29. The method of claim 28 wherein the diisocyanate is an aliphatic diisocyanate.

30. The method of claim 25 wherein the chain extender is biocompatible.

31. The method of claim 29 wherein the diisocyanate is 1,4-diisocyanatobutane, 1,2-diisocyanatoethane, lysine ester diisocyanate, 1,5-diisocyanatopentane, or any combination of these.

32. The method of claim 30 wherein the chain extender comprises an alcohol-amine, a diamine, a diol, or any combination of these.

33. The method of claim 32 wherein the diamine or diol is 1,4-butanediamine, Lysine Ester, 1,2-ethanediamine, Arginine Ethyl Ester, 1,5-pentanediamine, 1,3-propanediol, 1,2-propanediol, 1,4-butanediol, 1,6-hexanediol, 1,10-decanediol, cyclohexanedimethanol, and poly(caprolactone) diol, 1,5-pentanediol, 1,4-cyclohexanediol, 1,7-heptanediol, 1,8-octanediol, 1,9-nonanediol, 1,12-dodecanediol, caprolactone diol, or any combination of these.

34. The method of claim 25 wherein the biobeneficial moiety is poly(ethylene glycol), poly(propylene glycol), polyethylene oxide, PEO-PPO surfactants, PLURONIC surfactants, poly(tetramethylene glycol), amino-terminated PEG, hydroxy functional poly(vinyl pyrrolidone), dextran, dextrin, sulfonated dextran, dermatan sulfate, Silk-elastin protein block-copolymers, sodium hyaluronate, hyaluronic acid, poly(2-hydroxyethyl methacrylate), dihydroxy poly (styrene sulfonate), poly(3-hydroxypropyl methacrylate), poly(3-hydroxypropyl methacrylamide), poly(alkoxy methacrylates), poly(alkoxy acrylates), polyarginine peptides (PAP), phosphoryl choline, heparin, chondroitin sulfate, glycosaminoglycans, chitosan, polyethylene oxide, or any combination of these.

35. A polymer blend comprising at least two different type-one polymers,
wherein type-one polymers are the compositions of claim 1.

36. A polymer blend comprising
at least one type-one polymer, wherein type-one polymers are the compositions of claim 1; and
the type-two polymer, wherein the type-two polymer is a biocompatible polymer different from the at least one type-one polymer.

37. The polymer blend of claim 36 wherein type-two polymers are polycaprolactone, poly(D,L-lactide), poly(L-lactide), poly(D,L-lactide-co-L-lactide), poly(glycolide), poly(D,L-lactide-co-glycolide), poly(dioxanone), poly(4-hydroxybutyrate), poly(3-hydroxybutyrate), poly(3-hydroxy valerate), poly(hydroxybutyrate-co-hydroxyvalerate), poly(tyrosine derive carbonates), poly(tyrosine arylates), poly(imino carbonates), poly(trimethylene carbonate), poly(anhydrides), poly(orthoesters), poly(ester amides) or their mixtures.

* * * * *